(12) United States Patent
Patel (10) Patent No.: US 9,060,620 B1
(45) Date of Patent: Jun. 23, 2015

(54) BABY RESTRAINING ARTICLE

(71) Applicant: Yogi Realty LLC, Phoenix, AZ (US)

(72) Inventor: Apoorva Patel, Phoenix, CA (US)

(73) Assignee: YOGI REALTY LLC, Phoenix, AZ (US)

( * ) Notice: Subject to any disclaimer, the term of this patent is extended or adjusted under 35 U.S.C. 154(b) by 0 days.

(21) Appl. No.: 14/096,581

(22) Filed: Dec. 4, 2013

(51) Int. Cl.
*A47D 15/00* (2006.01)
*A61F 5/37* (2006.01)

(52) U.S. Cl.
CPC ............... *A47D 15/008* (2013.01); *A61F 5/37* (2013.01)

(58) Field of Classification Search
CPC ................................ A47D 15/008; A61F 5/37
USPC .............. 5/424, 494, 655, 497, 947; 128/872, 128/875, 876
See application file for complete search history.

(56) References Cited

U.S. PATENT DOCUMENTS

| | | | |
|---|---|---|---|
| 648,621 A | 5/1900 | Hopper | |
| 1,320,032 A | 10/1919 | Bailey | |
| 1,502,276 A | 7/1924 | Siebert | |
| 1,639,424 A | 8/1927 | Breslin | |
| 1,923,809 A | 8/1933 | Bates | |
| 2,553,007 A | 5/1951 | Rosenthal | |
| 2,623,678 A | 12/1952 | Law | |
| 2,642,865 A | 6/1953 | McGann et al. | |
| 2,758,595 A * | 8/1956 | Lovett | 5/655 |
| 2,850,746 A | 9/1958 | Foehner | |
| 3,987,505 A * | 10/1976 | Hickey | 2/114 |
| 5,400,803 A * | 3/1995 | Vines | 128/872 |
| D382,642 S | 8/1997 | Van Gisbergen Rutherford | |
| 6,708,356 B1 * | 3/2004 | LaValle | 5/655 |
| 6,834,405 B1 * | 12/2004 | Hillstead | 5/655 |
| 7,111,344 B2 * | 9/2006 | French | 5/494 |
| 7,150,054 B1 * | 12/2006 | Byrne et al. | 5/494 |
| 7,337,481 B2 | 3/2008 | Gilbert et al. | |
| 7,603,732 B2 * | 10/2009 | Robles et al. | 5/655 |
| 8,032,961 B1 * | 10/2011 | Downs | 5/655 |
| 2003/0154549 A1 | 8/2003 | Landry | |
| 2009/0241261 A1 | 10/2009 | Sack | |
| 2009/0313757 A1 * | 12/2009 | Walsh-Barltrop | 5/424 |

\* cited by examiner

*Primary Examiner* — Michael Trettel
(74) *Attorney, Agent, or Firm* — Precision IP

(57) ABSTRACT

An article or apparatus is described for restraining a baby. The article may include a special-purpose sheet, restraint(s) such as strap(s) that are anchored to the sheet and/or to a mattress, and connector(s) such as buckle(s). The sheet is designed to have a plurality of attached bases that allow the restraints to be anchored to the sheet and/or to the mattress. The baby may be placed on the sheet on his back, the restraints may be lightly tightened around the baby, and the connectors at the ends of the restraints may join to lock the baby on his back. The connectors may then be unlocked in the morning so that the baby may be safely retrieved from the sheet. The sheet may also include strap(s) that wrap around the mattress and connect in the front or back.

23 Claims, 8 Drawing Sheets

TOP VIEW OF SHEET OR MATTRESS

TOP VIEW OF SHEET OR MATTRESS

FIG. 1
TOP VIEW OF SHEET OR MATTRESS

FIG. 2
TOP VIEW OF SHEET OR MATTRESS

FIG. 3 BOTTOM VIEW OF SHEET

FIG. 4
BOTTOM VIEW OF SHEET

FIG. 6 BOTTOM VIEW OF MATTRESS

FIG. 7
BOTTOM VIEW OF MATTRESS

FIG. 8
TOP VIEW OF SHEET OR MATTRESS

BABY RESTRAINING ARTICLE

TECHNICAL FIELD

The technical field relates to articles for restraining a baby.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Sudden Infant Death Syndrome (SIDS) is the leading cause of death for infants 1 month to 1 year old, claiming the lives of about 2,500 babies each year in the United States. The best known way to reduce the risk of SIDS is to place babies to sleep on their backs.

Unfortunately, SIDS can affect babies even if they have been placed to sleep on their backs. As babies grow older and get stronger, they gain the ability to flip themselves over from their backs to their stomachs, but they may not be able to repeat the feat to return to their backs. For this reason, parents restlessly spend countless hours checking on their babies to ensure that they have not flipped over on their stomachs. Parents deserve better options, and so do their children.

DETAILED DESCRIPTION

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

GENERAL OVERVIEW

An article or apparatus is described for restraining a baby. The article may include a special-purpose sheet, restraint(s) such as strap(s) that are anchored to the sheet and/or to a mattress, and a connector or connector portion(s) such as a buckle or different parts of buckle(s). The sheet is designed to have a plurality of attached bases that allow the restraints to be anchored to the sheet and/or to the mattress. The baby may be placed on the sheet on his back, the restraints may be lightly tightened around the baby, and the connector portion(s) at the ends of the restraints may join to lock the baby on his back. The connector portion(s) may then be unlocked in the morning so that the baby may be safely retrieved from the sheet. The sheet could but does not need to be attached to the frame of a crib, and the sheet could but does not even need to be affixed to the mattress. Instead, the sheet may be fitted to elastically hug the mattress. The sheet may also include strap(s) that wrap around the mattress and connect in the front or back of the mattress, behind the sheet.

In one embodiment, the article includes a sheet, a plurality of bases attached to the sheet, and a plurality of restraint portions adapted to restrain a baby. In another embodiment, the sheet that is specialized with bases is sold separately from the restraints, and multiple different types of restraints may be interchangeable. For example, a swaddling-type restraint may be changed in for or changed out from a strap-type restraint. In yet another embodiment, the sheet, restraint portion(s), and/or mattress are sold together. The sheet may be affixed to the mattress or may be removably attached to the mattress.

In one embodiment, the article comprises a sheet, a plurality of bases attached to the sheet, a plurality of restraint portions adapted to restrain the baby, and a connector adapted to connect the plurality of restraining portions. The plurality of bases may include a first base attached to the sheet in a first direction from a region of the sheet, a second base attached to the sheet in a second direction from the region, and a third base attached to the sheet in a third direction from the region. For example, the different directions may include to the left of the region, to the upper left of the region, above the region, to the upper right of the region, to the right of the region, to the lower right of the region, below the region, and/or to the lower left of the region. The plurality of restraint portions may include a first restraint portion in contact with the first base, a second restraint portion in contact with the second base, and a third restraint portion in contact with the third base. For example, the restraint portions may be slidably held by or attached to their respective bases. The article may further include additional base(s), such as a fourth base in a fourth direction of the region and a fifth base in a fifth direction of the region. The additional base(s) may hold additional restraint portions such as a fourth restraint portion and fifth restraint portion, respectively.

To simplify various examples, the first direction from the region is described as a direction to the left of the sheet, the second direction from the region as a direction to the right of the region, and the third direction from the region as a direction below the region. Other combinations of the example directions from the region are also possible and may be substituted for the left, right, and lower directions in the various examples.

Figure 1:
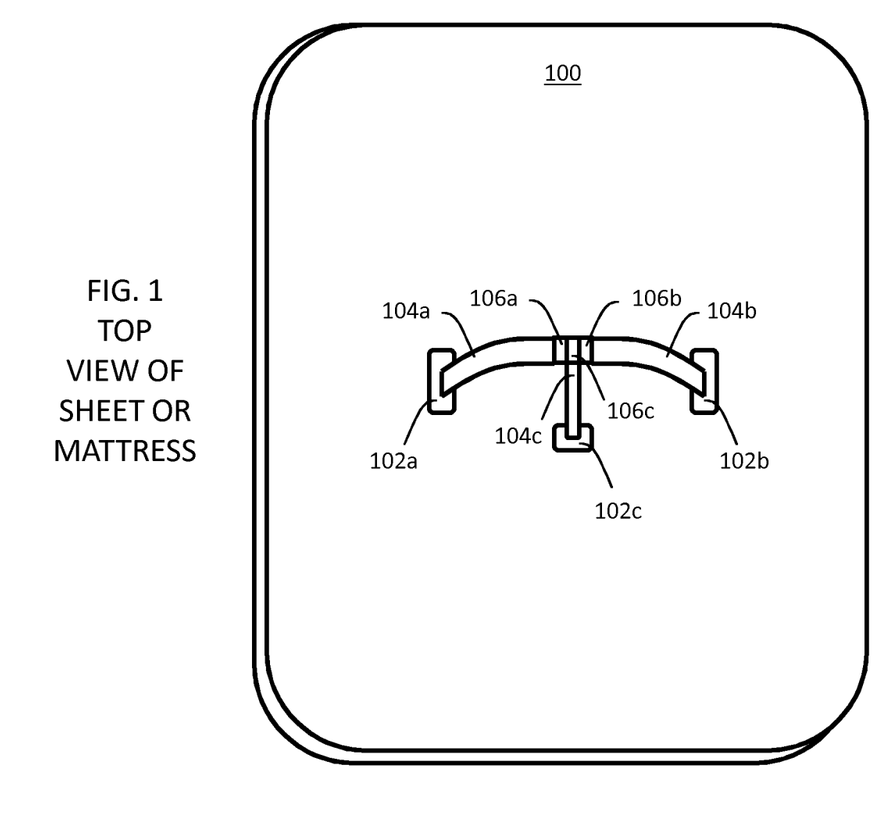
FIG. 1 illustrates a top view of an example sheet or mattress with a left restraint, a right restraint, and a lower restraint for restraining a baby lying on top of the sheet.

FIG. 1 illustrates a top view of an example sheet or mattress 100 with a left restraint 104a, a right restraint 104b, and a lower restraint 104c for restraining a baby lying on top of the sheet. The left restraint 104a passes through or is attached to left base 102a. Similarly, right restraint 104b passes through or is attached to right base 102b, and lower restraint 104c passes through or is attached to lower base 102c. The bases 102a, 102b, and 102c are attached to or otherwise part of sheet or mattress 100. The restraints 104a, 104b, and 104c meet at a connector defined by connector portions 106a, 106b, and 106c. As shown, left connector portion 106a is at the end of left restraint 104a, and right connector portion 106b is at the end of right restraint 104b. If the connector is a T connector, left connector portion 106a and right connector portion 106b may snap into lower connector portion 106c.

In the example of FIG. 1, a baby's back may be placed in a region spanning between left base 102a and right base 102b, and the restraints may be lifted around the baby and secured at connector portions 106.

Example Bases

The plurality of bases may include any combination of:
  left base(s) attached to the sheet at first point(s) that lie to the left of a region of the sheet,
  right base(s) attached to the sheet at second point(s) that lie to the right of the region,
  lower base(s) attached to the sheet at third point(s) that lie below the region, and/or
  upper base(s) attached to the sheet at fourth point(s) that lie above the region.

For example, the region may be an area on the sheet designated for the baby's back, and a base may be at or near any border of the region. In one example, the base is attached to the sheet as a border for an opening such as a hole or slot through which a restraint may pass. In this example, the base may strengthen the sheet by adding layers of same or different material than the sheet itself. For example, the sheet may be cotton, polyester, or rayon (or any other material suitable for a baby's bedsheets), and the base may be made of the same material or additional material that could be sturdier, such as nylon, leather, or plastic. The base may be attached to the sheet by sewing, stapling, tying, sticking, taping, or gluing the material to the sheet or by any other means that fixes the base to the sheet to resist or distribute sliding or pulling forces between the restraint and the base. The base itself may even just be added threading around the opening that serves to strengthen the opening and allow a restraint to pass through the opening, and possibly slide and be pulled without tearing the sheet.

In one embodiment, the sheet, bases, and restraint portions are made out of machine-washable materials such that the entire sheet, with or without restraint portions intact, is machine washable in a standard washing machine. In another embodiment, the sheet and bases may be machine-washable, and the restraint portions may be rinsed in water or spot-cleaned. In yet another embodiment, the entire article may be rinsed in water or spot-cleaned.

In another example, the base is attached to the sheet as a mount to which the restraint may be attached. The base may be made of similar materials as in the other embodiment, with a goal of distributing the force that could be provided when a restraint is slid or pulled by the baby. The restraint may be attached to the restraint using threading, staples, a hook-and-loop fastener such as Velcro, tape, glue, or any other means that fixes the restraint to the base to resist or distribute sliding or pulling forces between the restraint and the base.

Example Restraint Portions

The plurality of restraint portions may be held, slidably or fixedly, by the plurality of bases, and the plurality of restraint portions may be distinct parts of one or multiple restraints. For example, a restraint portion may be sewed or otherwise attached to a respective base. In another example, a restraint portion may slidably fit through a respective base. In the latter example, the base may be a reinforced hole in the sheet. The plurality of restraint portions may include any combination of:
  left restraint(s) held by the left base(s),
  right restraint(s) held by the right base(s),
  lower restraint(s) held by the lower base(s), and/or
  upper restraint(s) held by the upper base(s).

For example, a base may have an opening such as a hole or slot through which a restraint portion such as part of a strap may pass. In the example, the base may hold one end of the part of the strap within the hole or slot but allow the strap to otherwise move freely. The strap may continue behind the sheet and pass back through another opening to form another restraint portion. In this example, a portion of the strap may be stitched into the back of the sheet, pass behind the sheet, or even wrap around the mattress.

If a portion of the strap is behind the sheet, a majority or minority, in terms of surface area, of that portion may be stitched into the sheet. In a particular example, the strap comprises:
  a first restraint portion in front of the sheet, such as a left restraint portion,
  a strap portion below the sheet, and
  a second restraint portion in front of the sheet, such as a right restraint portion.

Figure 4:
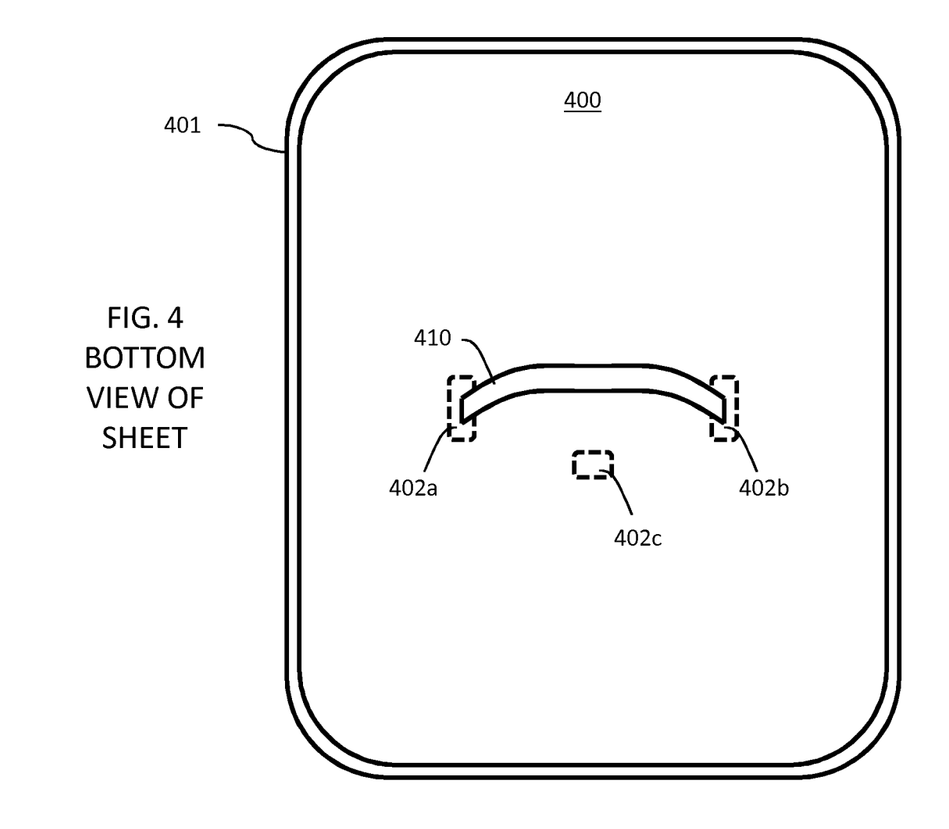
FIG. 4 illustrates a bottom view of an example sheet, such as the sheet of FIG. 1, where a single strap portion wraps behind a baby lying on top of the sheet.

FIG. 4 illustrates a bottom view of an example sheet 400, such as the sheet of FIG. 1, where a single strap portion 410 wraps behind a baby lying on top of the sheet. Also as shown, bases 402a, 402b, and 402c may include stitching or other material that is not visible from the top of the sheet, or may be missing stitching or other material that is visible from the top of the sheet.

In one embodiment, whether a strap portion is stitched behind the sheet, merely passes behind the sheet, or wraps around the mattress, the strap portion may comprise multiple parts that connect together. For example, the strap portion may include two or more strap portions that connect together with a buckle behind the sheet or even below the mattress. In a particular example, the strap portions meet under the mattress and terminate in connector portions that snap together.

Figure 3:
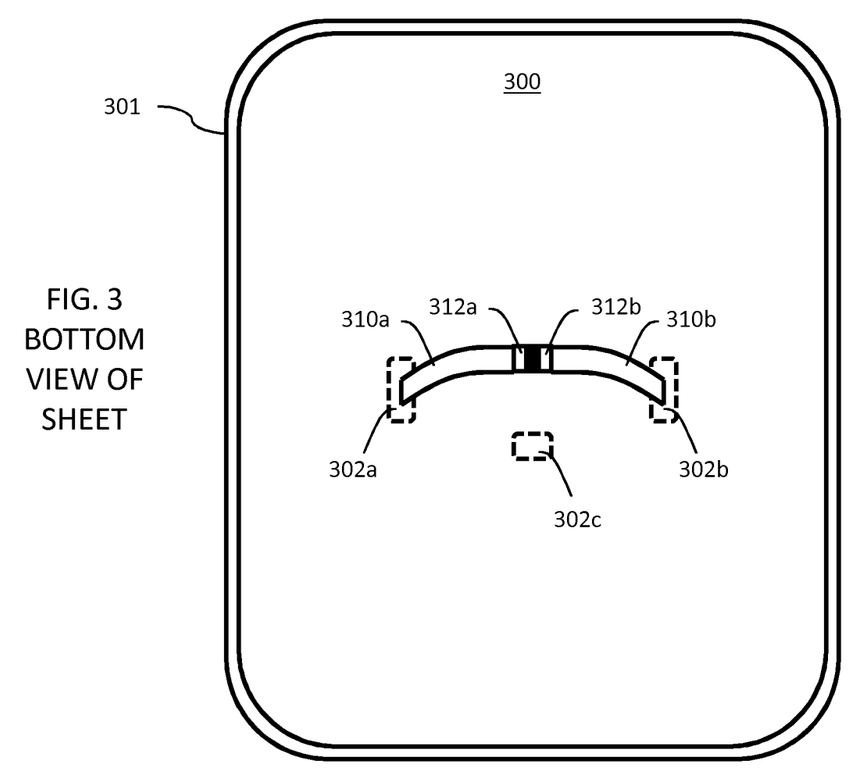
FIG. 3 illustrates a bottom view of an example sheet, such as the sheet of FIG. 1, where strap portions connect behind a baby lying on top of the sheet.

FIG. 3 illustrates a bottom view of an example sheet, such as the sheet of FIG. 1, where strap portions 310a and 310b connect behind a baby lying on top of the sheet. As shown, sheet 300 includes elastic portion 301 for fitting around a mattress. Left strap portion 310a attaches to or passes through sheet 300 and ends at connector portion 312a. Similarly, right strap portion 310b attaches to or passes through sheet 300 and ends at connector portion 312b. The connector portions 312 may snap or lock together behind the baby. As shown, bases 302a, 302b, and 302c may include stitching or material that may not be visible from the top of the sheet, or may be missing stitching or other material that is visible from the top of the sheet.

Figure 5:
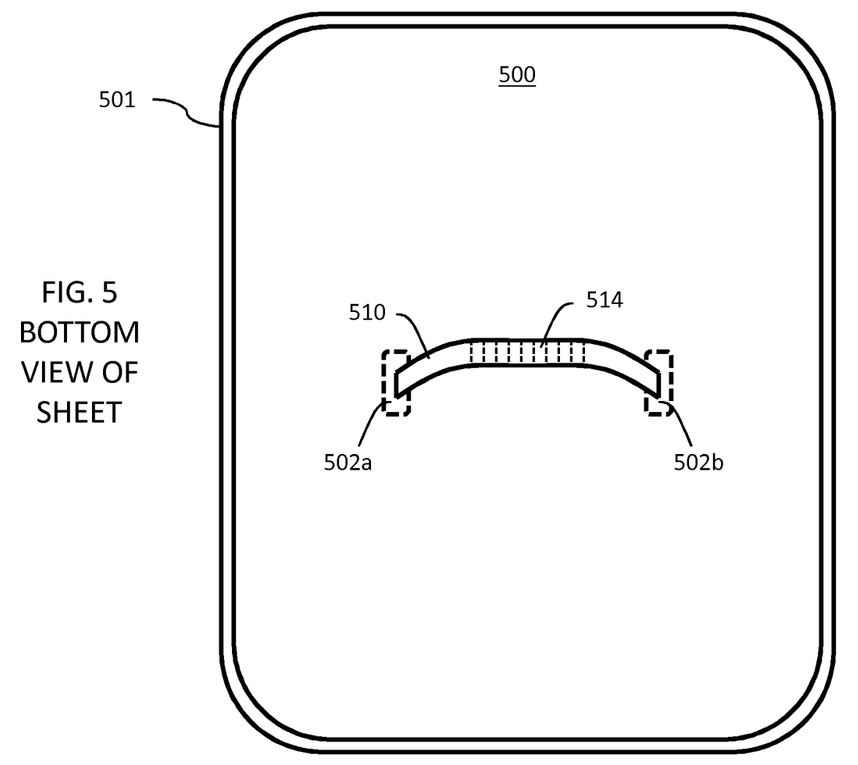
FIG. 5 illustrates a bottom view of an example sheet, such as the sheet of FIG. 1, where strap portion(s) are stitched into the back of the sheet.

FIG. 5 illustrates a bottom view of an example sheet, such as the sheet of FIG. 1, where strap portion(s) 510 are stitched to the back of the sheet at stitched portion 514.

Figure 6:
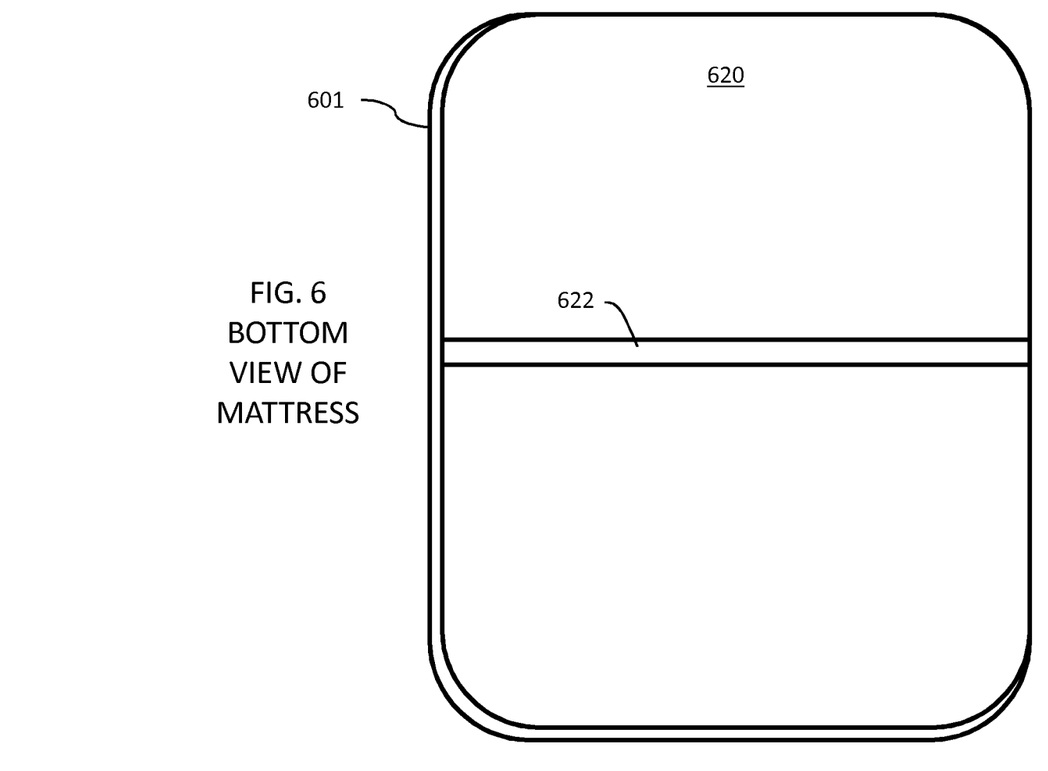
FIG. 6 illustrates a bottom view of a mattress where a strap wraps around the mattress from through and behind an example sheet.

FIG. 6 illustrates a bottom view of a mattress where a strap 622 wraps around the mattress from through and behind an example sheet. For example, strap 622 may originate from left strap portion 310a at one end and right strap portion 310b at the other end. Strap portions 310 are shown in FIG. 3. The strap portions may pass through or attach to the sheet at bases 302a and 302b, but, instead of connecting at connector portions 312a and 312b as shown in FIG. 3, the strap portions 310a and 310b wrap around the mattress behind the fitted sheet 601 and out from under the fitted sheet.

Figure 7:
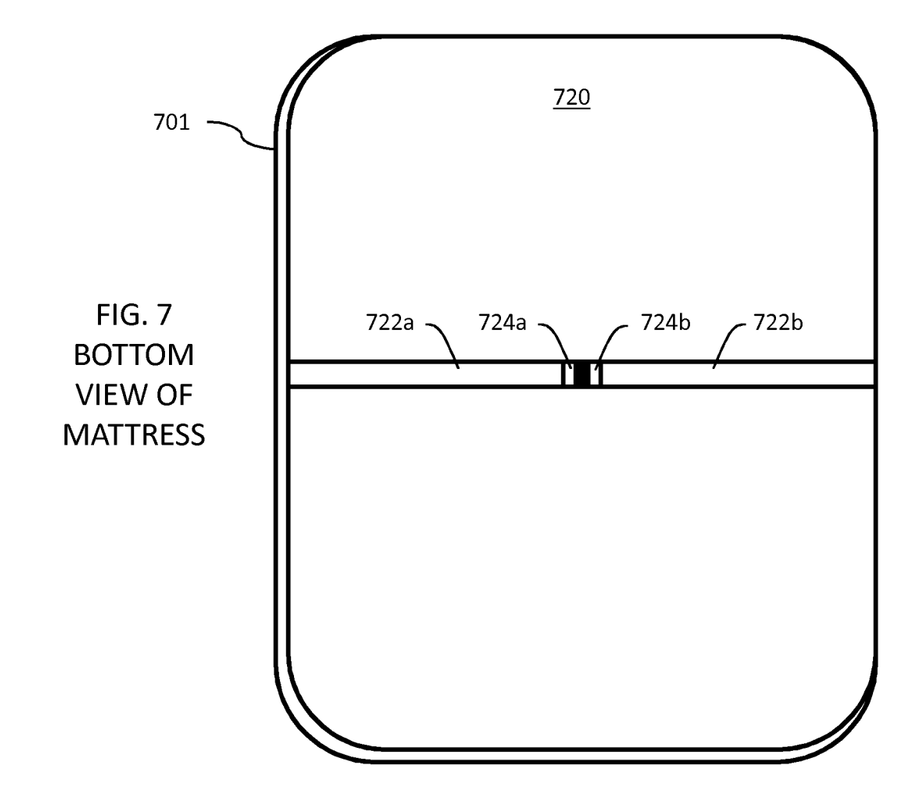
FIG. 7 illustrates a bottom view of a mattress where strap portions wrap around the mattress and connect in the back.

FIG. 7 illustrates a bottom view of a mattress where the strap portions 722a and 722b wrap around the mattress and connect in the back. Left strap portion 722a may wrap around mattress, under fitted sheet 701, and continue as left strap portion 310a to pass through or attach to the sheet at left base 302a. Similarly, right strap portion 722b may wrap around mattress, under fitted sheet 702, and continue as right strap portion 310b to pass through or attach to the sheet at right base 302b. Left strap portion 722a ends at connector portion 724a, which connects to connector portion 724b at the end of right strap portion 722b.

In another example, the base may be attached to the end of a restraint portion. In a particular example, one end of the strap may be stitched to the base, and the other end of the strap may be attached to a portion of a connector such as a buckle. In this example, the restraint portion terminates at the base at one end and at the connector at the other end. The restraint portion may also include additional slack that passes beyond either end or doubles a thickness of the restraint portion. The additional slack is used to adjust the restraint portion to be larger or smaller.

Some, none, or all of the restraint portion(s) may be adjustable to support babies of various sizes and various levels of comfort.

Example Connector Portions

The plurality of restraint(s) may connect using a connector comprising a plurality of connector portion(s) attached to the plurality of restraining portion(s). The plurality of connector portions may include any combination of:
- left connector portion(s) attached to the left restraining portion(s),
- right connector portion(s) attached to the right restraining portion(s),
- lower connector portion(s) attached to the lower restraining portion(s), and/or
- upper connector portion(s) attached to the upper restraining portion(s).

For example, a 3-point harness may have a buckle that connects a left strap portion, a right strap portion, and a lower strap portion. In another example, a 5-point harness may have a buckle that connects these strap portions and also a left shoulder strap portion and a right shoulder strap portion.

The connector may be any device that allows multiple restraint portions or strap portions to connect to each other, for example, to restrain a baby. In one embodiment, the connector is a T-connector, where the lower portion of the T-connector comprises a first insert that accepts the left connector portion from the left restraint portion and a second insert that accepts the right connector portion from the right restraint portion.

In another embodiment, the connector is a Y-connector, where any connector is adapted to be connected to any other connector, and the remaining connector may be snapped into place after the other connectors are already connected.

The restraint connector may also be a 2-way, 3-way, 4-way, 5-way, or n-way connector that secures n restraint portions that may be connected to n bases.

The connector may also connect strap portions that pass behind the sheet or behind the mattress.

A single connector function, such as securing a baby with restraint portions, may be accomplished by multiple connectors working together whether or not they are physically connected to each other. For example, an upper connector may be used to connect upper restraints for an upper body of the baby, and a lower connector may be used to connect lower restraints for a lower body of the baby.

In one embodiment, the connector is lockable and unlockable with the press of a button or the flip of a mechanical switch. The lock may be baby-proof such that the lock requires the strength or precision of an adult to operate. For example, the connector may be locked by snapping in at least one of the connector portions on at least one of the restraints to at least one other of the connector portions on at least one other of the restraints. The connector may be unlocked by snapping out at least one of the connector portions from at least one other of the connector portions. The connector portions may be locked and unlocked one portion at a time or all at once.

In one embodiment, the connectors are plastic portions molded to fit together snugly. The plastic portions may be flexible enough to snap into a locked connection, but rigid enough to remain in the locked connection until they are unlocked. The connectors may also be made of fabric, metal, or any other material that is safe for use near or on a baby.

In one embodiment, the connector is lockable and unlockable using one or more sets of hook fasteners and one or more sets of loop fasteners. For example, one restraint portion may have a set of hook fasteners attached to the end, and another restraint portion may have a set of loop fasteners attached to the end. The hook fasteners may lock into the loop fasteners and require an adult-level of force to unlock. In a particular example, the hook-and-loop fasteners are Velcro® fasteners.

Non-Strap Restraint Examples

Various examples are described herein with respect to strap-like restraints, such as bands or cords. However, the examples are not limited to these types of restraints. In one embodiment, at least a subset of the restraint portions are sheets of fabric adapted to swaddle a baby in the region. For example, the restraint sheets may be supported by a wide base that stretches the sheet from the baby's lower to middle region up to the baby's chest or shoulders. The restraint sheets may snap together with plastic connectors at the end, or the sheets may merely tie together with or without any specialized connector.

In the same or a different embodiment, a lower restraint portion may include one or more stitched pockets adapted to cover legs of a baby. The pockets may be long enough to support babies of a variety of sizes. The back and bottom of a baby may be placed in a resting region of the sheet just above the pockets, and the legs of the baby may be inserted into the pockets. The sheet may support one or two pockets, depending on parents' and babies' preferences. The pockets may be loosely fitted to allow the baby to move his or her legs comfortably, but tight enough to prevent tangling of the fabric that lines the pocket.

Figure 8:
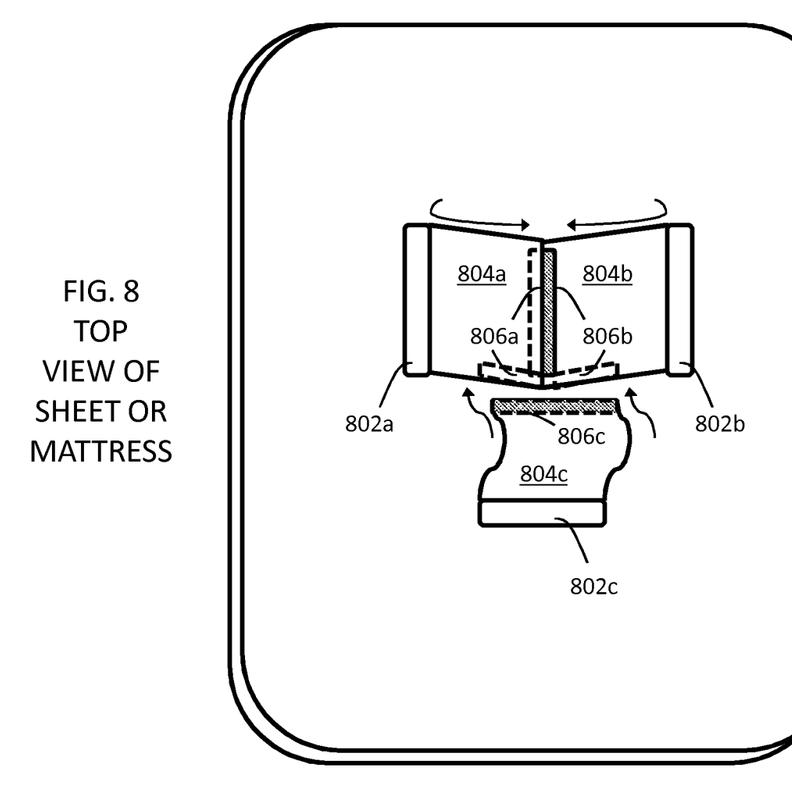
FIG. 8 illustrates a top view of an example sheet or mattress where the restraints are adapted to swaddle a baby.

FIG. 8 illustrates a top view of an example sheet or mattress where the restraints are adapted to swaddle a baby. As shown, lower restraint portion 804c is a sheet that spans from elongated lower base 802c upwardly. Lower restraint portion 804c may span up to a mid-region of the baby or to a chest region of the baby.

Also as shown, right restraint portion 804b is a sheet that spans from elongated right base 802b toward left base 802a. As shown, right connector portion 806b connects to lower connector portion 806c. For example, the connector portions 806a and 806b may be hook-and-loop connectors, or snap-on button connectors, or slide-in button connectors, which work well for fabric-to-fabric connections.

Left restraint portion 804a is also a sheet that spans from elongated left base 802a toward right base 802b. The restraint portions 804a and 804b may connect at connector portions 806a and 806b. As shown, restraint portion 804c lies on the bottom, followed by right restraint portion 804b and then by left restraint portion 804a; however, the sheets may be layered in any order or may connect without forming layers.

Pillow Examples

In one embodiment, base(s) may also be adapted to attach to pillow(s). For example, the pillow base(s) may be located just above the region in which the baby's back or either shoulder is placed. In this manner, a pillow base may be centered to provide general comfort for the back of the head or offset from the center to force a tilting of the head. The pillow(s) may be used to prop or tilt the baby's head partially to one side or the other while the baby is lying on his or her back. The baby's head may be tilted to avoid developing a flatness on the back of the baby's head, which may result from the baby spending too much time on his or her back. A single sheet may include a left pillow base and a right pillow base for alternately holding a pillow attachment. A pillow may be placed on the left pillow base some nights to encourage the baby to tilt his head away from that side, and on the right pillow base other nights to encourage the baby to tilt his head away from that side.

In one embodiment, a pillow is adapted to be wedge-shaped or flat-bottomed such that the pillow sits firmly on the sheet. The pillow may or may not be attached to a pillow base, and the sheet may or may not have a pillow base even if the pillow is used.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

Figure 2:
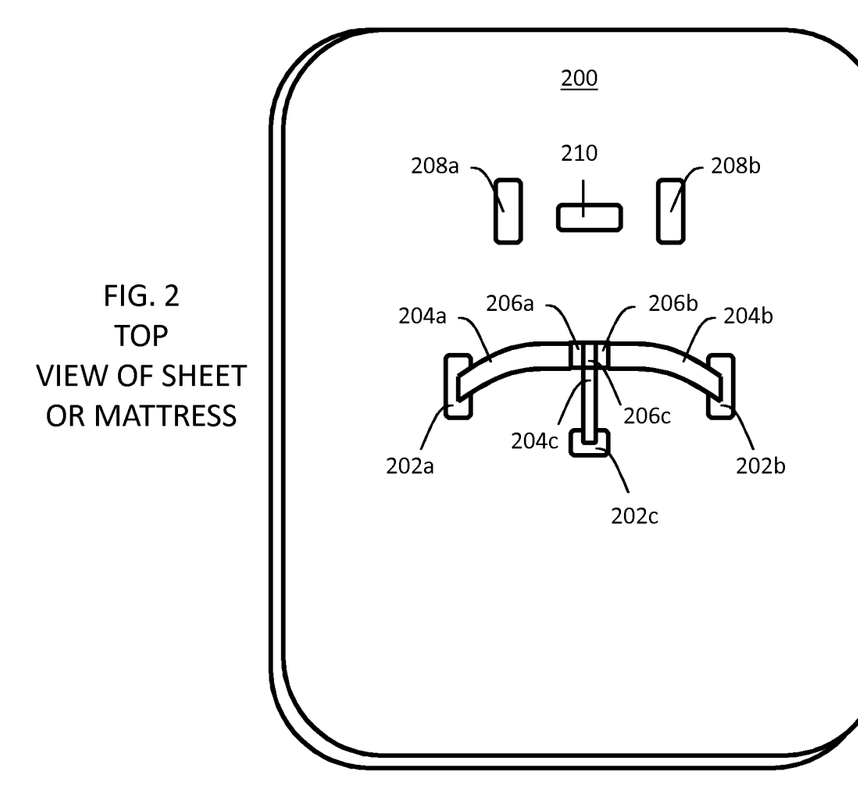
FIG. 2 illustrates a top view of an example sheet or mattress with upper bases that may hold pillows, head tilting objects, and/or shoulder restraints.

FIG. 2 illustrates a top view of an example sheet or mattress with upper bases that may hold pillows, head tilting objects, and/or shoulder restraints. As shown, left upper base 208a and right upper base 208b may be used to mount head tilting objects, such as soft wedges, or shoulder restraints, which, if present, would connect to connector portions 206. For example, a single removable pillow may be attached to either left upper base 208a or right upper base 208b, which may both be present on the product. The pillow may be switched from one base to the other to balance the baby's sleeping positions. Also as shown, central upper base 210 may hold a pillow. The pillow may be designed to be concave to cradle the baby's head or neck. By cradling the head, the pillow may reduce the likelihood of the baby forming a flatness on the back of his or her head.

What is claimed is:

1. An article for restraining a baby, the article comprising:
   a sheet;
   a plurality of bases attached to the sheet, the plurality of bases comprising:
      a first base attached to the sheet in a first direction from a region of the sheet,
      a second base attached to the sheet in a second direction from the region, and
      a third base attached to the sheet in a third direction from the region;
   a plurality of restraint portions adapted to restrain a baby, the plurality of restraint portions comprising:
      a first restraint portion in contact with the first base;
      a second restraint portion in contact with the second base;
      a third restraint portion in contact with the third base; and
   a connector adapted to connect the plurality of restraining portions;
   wherein the plurality of bases comprise pieces of material, in addition to the sheet, that are stitched to a back of the sheet.

2. An article for restraining a baby, the article comprising:
   a sheet;
   a plurality of bases attached to the sheet, the plurality of bases comprising:
      a first base attached to the sheet in a first direction from a region of the sheet,
      a second base attached to the sheet in a second direction from the region, and
      a third base attached to the sheet in a third direction from the region;
   a plurality of restraint portions adapted to restrain a baby, the plurality of restraint portions comprising:
      a first restraint portion in contact with the first base;
      a second restraint portion in contact with the second base;
      a third restraint portion in contact with the third base; and
   a connector adapted to connect the plurality of restraining portions;
   a strap comprising:
      the first restraint portion in front of the sheet,
      the second restraint portion in front of the sheet, and
      a strap portion behind the sheet that meets the first restraint portion at one end of the strap portion and the second restraint portion at another end of the strap portion.

3. The article of claim 2, wherein the strap is adapted to wrap around a mattress.

4. The article of claim 2, wherein a majority of the strap portion is attached to a back of the sheet.

5. The article of claim 1, wherein at least one of the plurality of restraint portions is attached to and terminates at a respective base of the plurality of bases.

6. The article of claim 1, wherein the first restraint portion and the second restraint portion comprise sheets of fabric adapted to swaddle a baby in the region.

7. The article of claim 1, wherein the third restraint portion comprises one or more stitched pockets adapted to cover legs of a baby.

8. The article of claim 1, wherein at least one of the first restraint portion, the second restraint portion, or the third restraint portion is adjustable.

9. The article of claim 1, wherein the connector comprises:
   a first connector portion attached to the first restraining portion,
   a second connector portion attached to the second restraining portion, and
   a third connector portion attached to the third restraining portion;
   wherein the connector is lockable by snapping in at least one of the connector portions to at least one other of the connector portions and unlockable by snapping out at least one of the connector portions from at least one other of the connector portions.

10. The article of claim 1, wherein the sheet is elastically fitted for a crib mattress.

11. The article of claim 1, wherein the sheet is removable from a mattress and washable in a standard washing machine.

12. The article of claim 1, wherein the connector comprises:
    a left connector portion attached to the left restraining portion,
    a right connector portion attached to the right restraining portion, and
    a lower connector portion attached to the lower restraining portion.

13. The article of claim 1, wherein the first base is attached to the sheet to the left of the region, the second base attached is to the sheet to the right of the region, and the third base is attached to the sheet below the region.

14. The article of claim 1, wherein at least one of the restraining portions is attached to a respective base of the plurality of bases.

15. An article for restraining a baby, the article comprising:
    a sheet;
    a plurality of bases attached to the sheet, the plurality of bases comprising:
        a first base attached to the sheet in a first direction from a region of the sheet,
        a second base attached to the sheet in a second direction from the region, and
        a third base attached to the sheet in a third direction from the region;
    a plurality of restraint portions adapted to restrain a baby, the plurality of restraint portions comprising:
        a first restraint portion in contact with the first base;
        a second restraint portion in contact with the second base;
        a third restraint portion in contact with the third base; and
    a connector adapted to connect the plurality of restraining portions;
    wherein the first restraint portion comprises a first strap portion that passes through an opening in the first base; wherein the second restraint portion comprises a second strap portion that passes through an opening in the second base; and wherein the first strap portion meets the second strap portion behind the sheet.

16. The article of claim 15, wherein the connector is a first connector, and wherein the first strap portion meets the second strap portion at a second connector behind the sheet.

17. The article of claim 15, wherein the connector is a first connector, and wherein the first strap portion and the second strap portion are adapted to meet at a second connector behind a mattress.

18. An article for restraining a baby, the article comprising:
    a sheet;
    a plurality of bases attached to the sheet, the plurality of bases comprising:
        a first base attached to the sheet in a first direction from a region of the sheet,
        a second base attached to the sheet in a second direction from the region, and
        a third base attached to the sheet in a third direction from the region;
    a plurality of restraint portions adapted to restrain a baby, the plurality of restraint portions comprising:
        a first restraint portion in contact with the first base;
        a second restraint portion in contact with the second base;
        a third restraint portion in contact with the third base; and
    a connector adapted to connect the plurality of restraining portions;
    wherein the connector comprises:
        a first connector portion attached to the first restraining portion,
        a second connector portion attached to the second restraining portion, and
        a third connector portion attached to the third restraining portion;
    wherein the third connector portion comprises a first insert that accepts the first connector portion and a second insert that accepts the second connector portion.

19. An article for restraining a baby, the article comprising:
    a sheet;
    a plurality of bases attached to the sheet, the plurality of bases comprising:
        a first base attached to the sheet in a first direction from a region of the sheet,
        a second base attached to the sheet in a second direction from the region, and
        a third base attached to the sheet in a third direction from the region;
    a plurality of restraint portions adapted to restrain a baby, the plurality of restraint portions comprising:
        a first restraint portion in contact with the first base;
        a second restraint portion in contact with the second base;
        a third restraint portion in contact with the third base; and
    a connector adapted to connect the plurality of restraining portions;
    wherein the connector comprises:
        a first connector portion attached to the first restraining portion,
        a second connector portion attached to the second restraining portion, and
        a third connector portion attached to the third restraining portion;
    wherein all of the connector portions are adapted to lock together in a locked position.

20. An article for restraining a baby, the article comprising:
    a sheet;
    a plurality of bases attached to the sheet, the plurality of bases comprising:
        a first base attached to the sheet in a first direction from a region of the sheet,
        a second base attached to the sheet in a second direction from the region, and
        a third base attached to the sheet in a third direction from the region;
    a plurality of restraint portions adapted to restrain a baby, the plurality of restraint portions comprising:
        a first restraint portion in contact with the first base;
        a second restraint portion in contact with the second base;
        a third restraint portion in contact with the third base; and
    a connector adapted to connect the plurality of restraining portions;
    wherein the connector is lockable by one or more sets of hook fasteners and one or more sets of loop fasteners.

21. An article for restraining a baby, the article comprising:
    a sheet;

a plurality of bases attached to the sheet, the plurality of bases comprising:
  a first base attached to the sheet in a first direction from a region of the sheet,
  a second base attached to the sheet in a second direction from the region, and
  a third base attached to the sheet in a third direction from the region;
a plurality of restraint portions adapted to restrain a baby, the plurality of restraint portions comprising:
  a first restraint portion in contact with the first base;
  a second restraint portion in contact with the second base;
  a third restraint portion in contact with the third base; and
a connector adapted to connect the plurality of restraining portions;
wherein the plurality of bases comprise one or more pillow bases above the region, wherein each pillow base of the one or more pillow bases is adapted to hold a head pillow.

22. An article for restraining a baby, the article comprising:
a sheet;
a plurality of bases attached to the sheet, the plurality of bases comprising:
  a first base attached to the sheet in a first direction from a region of the sheet,
  a second base attached to the sheet in a second direction from the region, and
  a third base attached to the sheet in a third direction from the region;
a plurality of restraint portions adapted to restrain a baby, the plurality of restraint portions comprising:
  a first restraint portion in contact with the first base;
  a second restraint portion in contact with the second base;
  a third restraint portion in contact with the third base; and
a connector adapted to connect the plurality of restraining portions;
wherein the plurality of bases further comprise:
  a fourth base attached to the sheet in a fourth direction from the region, and
  a fifth base attached to the sheet in a fifth direction from the region;
and wherein the plurality of restraining portions further comprise:
  a fourth restraining portion held by the fourth base, and
  a fifth restraining portion held by the fifth base.

23. An article for restraining a baby, the article comprising:
a sheet;
a plurality of bases attached to the sheet, the plurality of bases comprising:
  a first base attached to the sheet in a first direction from a region of the sheet,
  a second base attached to the sheet in a second direction from the region, and
  a third base attached to the sheet in a third direction from the region;
a plurality of restraint portions adapted to restrain a baby, the plurality of restraint portions comprising:
  a first restraint portion in contact with the first base;
  a second restraint portion in contact with the second base;
  a third restraint portion in contact with the third base; and
a connector adapted to connect the plurality of restraining portions;
wherein at least one of the restraining portions is slidably held by a respective base of the plurality of bases.

* * * * *